United States Patent [19]
Schwartz et al.

[11] Patent Number: 5,378,604
[45] Date of Patent: * Jan. 3, 1995

[54] OLIGONUCLEOTIDE PROBES FOR DETECTION OF PERIODONTAL PATHOGENS

[75] Inventors: Dennis E. Schwartz, Redmond; Roy H. Kanemoto; Susan M. Watanabe, both of Seattle; Kim Dix, Arlington, all of Wash.

[73] Assignee: MicroProbe Corporation, Bothell, Wash.

[*] Notice: The portion of the term of this patent subsequent to May 18, 2019 has been disclaimed.

[21] Appl. No.: 3,367

[22] Filed: Jan. 12, 1993

Related U.S. Application Data

[63] Continuation of Ser. No. 571,563, Aug. 29, 1990, Pat. No. 5,212,059, and a continuation-in-part of Ser. No. 142,106, Jan. 11, 1988, abandoned.

[51] Int. Cl.$^6$ .......................... C12Q 1/68; C12P 39/00; C12P 19/34; C07H 17/00
[52] U.S. Cl. ........................................... 435/6; 435/42; 435/170; 536/23.1; 536/24.3; 536/24.32; 935/77; 935/78; 935/79
[58] Field of Search ............................. 435/6, 42, 91.1; 536/24.32, 27, 23.1, 24.3; 935/77, 78, 79

[56] References Cited

FOREIGN PATENT DOCUMENTS 1215904 12/1986 Canada .
133671 3/1985 European Pat. Off. .
144914 6/1985 European Pat. Off. .
199439 10/1986 European Pat. Off. .
209702 1/1987 European Pat. Off. .

OTHER PUBLICATIONS

FEMS Microbiology Letters, vol. 43, No. 2, Aug. 1987, Amsterdam, The Netherlands, pp. 187–193, Haun, G. et al. 'Oligonucleotide probes for genus-, species- and subspecies-specific identification of representatives of the genus Proteus'.
Oral Microbiol. and Immunol. vol. 1, No. 1, Oct. 1986, Copenhagen DK, pp. 58–62 French, C. K. et al. 'Dna probe detection of periodontal pathogens'.
Chen, P., et al., "The Use of Monoclonal Antibodies to Detect *Bacteroides gingivalis* in Biological Samples," *Infect. Immun.* 54:798–803 (1986).
Gmur, R., et al., "Quantitative Monitoring of the Periodontal Pocket Flora with Monoclonal Antibodies," *J. Dent. Res.* vol. 6:120 (1987, Abstract).
Fine, D. H. and Mandel, I. D., "Indicators of Periodontal Disease Activity: An Evaluation," *J. Clin. Periodont.* 13:533–546 (1986).
Gobel, U. B., et al., "Oligonucleotide Probes Complementary to Variable Regions of Ribosomal RNA Discriminate between Mycoplasma Species," *J. Gen. Microbiol.* 133:1969–1974 (1987).
Chen, M., et al., "Development of DNA Probes for Oral Microorganisms," *Assoc. Adv. Dent. Res. Meetings*, Wash. D.C. (1986).
Savitt, E., et al., "Detection of *A. actinomycetemcomitans* in Plaque by RNA Probes," *Assoc. Adv. Dent. Res. Meetings*, Wash. D.C. (1986).
Chuba, P. J., et al., "Synthetic Oliodeoxynucleotide Probes for the Rapid Detection of Bacteria Associated with Human Periodontitis," *J. Gen. Microb.* 134:1931–1938 (1988).
Weisburg, W. G., et al., "Natural Relationship between (List continued on next page.)

Primary Examiner—Margaret Parr
Assistant Examiner—Miguel H. Escallon
Attorney, Agent, or Firm—Townsend and Townsend Khourie and Crew

[57] ABSTRACT

This invention relates to compositions of oligonucleotide probes for use in the detection of bacteria associated with medical disorders of the human mouth, wherein said probes consist essentially of a segment of nucleic acid capable of selectively hybridizing under hybridizing conditions, to the 16S or 23S ribosomal RNA [rRNA] of said bacteria. Methods for detection, as well as diagnostic kits for the assay of these bacterium, are also disclosed.

2 Claims, No Drawings

OTHER PUBLICATIONS

Bacteriodes and Flavobacteria," *J. of Bacteriol.* 164(1):230–236 (Oct., 1985).

Chen, K., et al., "Broad range DNA probes for detecting and amplifying eubacterial nucleic acids," *FEMS Microbiology Letters* 57:19–24 (1989).

Johnson, J. L., et al., "Ribosomal Ribonucleic Acid Homology among Species of the Genus Bacteroides," *Int. J. Syst. Bacteriol.* 36(1):71–79 (Jan. 1986).

Waterman, M. S., "Multiple sequence alignment by consensus," *Nucleic Acids Research* 14(22):9095–9102 (1986).

van Steenbergen, T. J. M., et al., "Deoxyribonucleic acid homologies among strains of *Bacteriodes melaninogenicus* and related species," *J. Applied Bacteriol.* 53:269–276 (1982).

Dewhirst, F. E., et al., "*Chromobacterium, eikenella, kingella, neisseria, simonsiella*, and *Vitreoscilla* Species Comprise a Major Branch of the Beta Group . . . ," *Int. J. Syst. Bacteriol.* 39(3):258–266 (Jul. 1989).

Walker, R. L., et al., "Deoxyribonucleic Acid Relatedness Among *Haemophilus somnus, Haemophilus agni, Histophilus ovis*, . . . ," *Int. J. Syst. Bacteriol.* 35(1):46–49 (Jan. 1985).

Chuba, P. J., et al., "Comparison of 16S rRNA Sequences from the Family Pasteurellaceae: Phylogenetic Relatedness by Cluster Analysis," *J. Gen. Microbiol.* 134:1923–1930 (1988).

Gray, M. W., et al., "On the evolutionary descent of organisms and organelles: a global phylogeny based on a highly conserved structural core in small subunit ribosomal RNA," *Nuc. Acids Res.* 12(14):5837–5852 (1984).

Lane, D. J., et al., "Rapid determination of 16S ribosomal RNA sequences for phylogenetic analyses," *Proc. Natl Acad. Sci. USA* 82:6955–6959 (Oct. 1985).

Escande, F., et al., "Deoxyribonnucleic Acid Relatedness Among Strains of *Actinobacillus* spp. and *Pasteurella ureae*," *Int. J. Syst. Bacteriol.* 34(3):308–315 (Jul. 1984).

Fox, G. E., et al., "Comparative Cataloging of 16S Ribosomal Ribonucleic Acid: Molecular Approach to Procaryotic Systematics," *Int. J. Syst. Bacteriol.* 27(1):44–57 (Jan. 1977).

OLIGONUCLEOTIDE PROBES FOR DETECTION OF PERIODONTAL PATHOGENS

This application is a continuation of U.S. patent application Ser. No. 07/571,563 filed on Aug. 29, 1990, now U.S. Pat. No. 5,212,059, which was originally filed under the PCT as WO89/06704 filed on Jan. 9, 1989 and is a continuation-in-part of U.S. patent application Ser. No. 07/142,106, filed Jan. 11, 1988, now abandoned.

BACKGROUND OF THE INVENTION

TECHNICAL FIELD OF THE INVENTION

This invention relates to compositions of oligonucleotide probes for use in the detection of bacteria associated with medical disorders of the human mouth, wherein said probes consist essentially of a segment of nucleic acid capable of selectively hybridizing under hybridizing conditions, to the 16S or 23S ribosomal RNA [rRNA] of said bacteria. Methods for detection, as well as diagnostic kits for the assay of these bacteria, are also disclosed.

Substantial evidence exists implicating plaque bacteria in the etiology of human periodontal disease, particularly gingivitis and periodontitis. As these diseases have been studied, increasingly sophisticated methods for detection, quantitation, and identification of specific oral bacteria and other infectious viruses and microorganisms have been developed. These improved methods have led to the identification of specific pathogenic bacteria playing a major role in the etiology of periodontal disease.

Human periodontal diseases constitute a major health-care problem in the United States. While epidemiologic surveys suggest that there may be a reduction of the proportion of Americans with gingivitis in recent years, the number of patients having some stage of the disease remains high. Furthermore, the proportion of adults, aged 18–79 years, with periodontal pockets appears to be relatively unchanged.

In the early 1970's, roughly 30 percent of Americans had significant periodontal disease problems by age 50, and by age 60, between 30 and 40 percent of all Americans had lost all of their teeth, primarily due to periodontal disease. At present, the exact proportion of persons with severe periodontal disease is unknown, but recent estimates are that 10–20 percent of the overall American population has periodontal disease serious enough to result in tooth loss. Coincidental with the disease is a significant relationship between the onset and course of the disease, and identifiable (suspect) pathogenic bacterial species.

Although the precise complex mechanisms involved in the pathogenesis of human periodontitis are still unclear, there is wide agreement that bacteria that colonize the gingival crevice area around the teeth are of primary etiologic importance. Within the past decade, researchers at several academic institutions have demonstrated that of the large number of bacterial genera and species found in the human periodontal crevice or pocket (ca. 256 species), a relatively limited number of these appear to be consistently associated with periodontal disease. These microorganisms have been designated "suspect periodontal pathogens." Of particular interest are the microorganisms shown in Table 1.

INFORMATION DISCLOSURE

The detection and characterization of the periodontal pathogenic bacteria present in a given periodontal pocket site are, by current methods, both time-consuming and expensive (e.g., microscopic, cultural, gas chromatographic and metabolic product analysis). Furthermore, highly trained individuals, with sophisticated laboratory equipment, are required. Most of the published studies on the microbiology of human periodontal diseases have been compromised by the enormous workload that must be accomplished to isolate and characterize individual members of the microflora at each periodontal site. As a result, the number of sites sampled per patient and the number of patients examined are limited. Clearly, the present methods do not allow routine testing of periodontal patients for the presence of pathogenic bacteria.

Immunoassays are reported as an alternative to the above detection methodologies. Fluorescent monoclonal antibodies to *Actinobacillus actinomycetemcomitans* (A.a.), *Bacteroides gingivalis* (B.g.), and *Bacteroides intermedius* (B.i.) have been developed. Chen, P., et al., The Use Of Monoclonal Antibodies To Detect *Bacteroides gingivalis* In Biological Samples, Infection and Immunity, 54:798–803 (1986); Gmur, R., et al., Quantitative Monitoring Of The Periodontal Pocket Flora With Monoclonal Antibodies, Journal of Dental Research Vol. 66:120 (1987, abstract); Fine, D. H. and Mandel, I. D. Indicators Of Periodontal Disease Activity: An Evaluation, J. Clin. Periodontal, 13:533–546 (1986). These antibodies can be used directly on plaque smears on microscope slides. The testing requires manual counting of fluorescent bacteria on individual microscope slides, a procedure which is very labor-intensive and requires an expensive fluorescent microscope.

The potential for using nucleic acid hybridization technology to detect pathogenic bacteria is known and, more specifically, the use of rRNA for hybridization assays is known (Canadian Patent No. 1,215,904 and Oligonucleotide Probes Complementary to Variable Regions of RibosomalRNA Discriminate between Mycoplasma Species. J. General Microbiology (1987) 133, 1969–1974. U. B. Gobel, A. Geiser, E. J. Startbridge). Whole genomic DNA probes have reportedly been used to identify periodontal pathogens (EP 199,439), but these methods do not possess the hybridization specificity of the disclosed invention. For example, fragments of A.a., B.g., or B.i. genomic DNA have been cloned into the pSP64 transcription vector. chen, M., et al., Development Of DNA Probes For Oral Microorganisms, Assoc. Adv. Dental Res. Meetings, Washington, D.C. (1986); Savitt, E., et al., Detection of *A. actinomycetencomitans* In Plaque By RNA Probes, Assoc. Adv. Dental Res. Heelings, Washington, D.C. (1986). The pSP64 vector is used to produce A.a, B.g., or B.i. RNA transcripts. A pSP64-A.a. probe was reported to be specific when tested against pure cultures or plaque samples. However, pSP64-B.g. and pSP64-B.i. probes cross-hybridized slightly with some non-B.g. and non-B.i. bacteria, respectively. Since non-pathogenic Bacteroides species are abundant in the subgingival crevice, these cross-hybridizations may cause false positive identifications.

Each of the above methods of detecting periodontal pathogens lacks one or more of the following criteria necessary for a routine diagnostic assay: 1) cost (inexpensive); 2) batch capability; 3) speed (hours, not days or weeks); 4) sensitivity; 5) specificity; 6) multiple pathogen identification in one test; 7) simplicity; and 8) ability to detect both viable and nonviable organisms. Consequently, there is a need in the art for alternate detection methodologies.

SUMMARY OF THE INVENTION

The present invention is directed to compositions of oligonucleotide probes for the detection of bacteria associated with human oral medical disorders, wherein said probes comprise a segment of nucleic acid capable of selectively hybridizing, under hybridizing conditions, to hypervariable regions of ribosomal RNA of the bacteria with the provision that any additional nucleotides covalently bound to said segment do not hybridize under said conditions to nucleic acids of bacteria commonly found in the human mouth. Functionally, these probes are able to hybridize to unique portions of the bacterial rRNA or corresponding genomic DNA permitting ready detection and identification of such bacteria without cross-reacting with other bacterial species. In addition, compositions of oligonuleotide probes directed to conserved regions of 16S and 23S ribosomal RNA are described, wherein said probes can be utilized as specific probes for ribosomal RNA or the corresponding genomic sequence, and can be used for sequencing of ribosomal nucleic acids.

This invention is also directed to a probe of the formula:

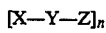

$$[X-Y-Z]_n$$

wherein:
a) X is a sequence of 0 to 100 nucleotides or nucleotide analogs that are non-homologous to conserved or non-conserved regions of bacterial nucleic acid found in bacteria inhabiting human mouths;
b) Y is a sequence of 10 to 100 nucleotides or nucleotide analogs that are capable of hybridizing under hybridizing conditions to hypervariable regions of the ribosomal RNA of bacteria inhabiting human mouths, such that Y may also comprise subsequences that are capable of hybridizing under hybridizing conditions to only one species of said bacteria, to two species of said bacteria or to three species of said bacteria;
c) Z is a sequence of nucleotides the same as or different from X, such that nucleotides or nucleotide analogs are non-homologous to conserved or non-conserved regions of nucleic acid of bacteria found inhabiting human mouths; and
d) n is 1–500, or more and, where n is greater than 1, Y can be the same or different sequences of nucleotides having said hybridization capability- The probe can be free or contained within a vector sequence (e.g., plasmids or Single Stranded DNA).

The following bacteria are of particular interest, because they have been found in association with periodontal disease: *Actinobacillus* (ex. Haemophilus) *actinomycetemcomitans; Bacteroides gingivalis; Bacteroides intermedius* Type 1; *Bacteroides intermedius* Type 2; *Eikenella corrodens; Bacteroides forsythus; Fusobacterium nucleatum; Fusobacterium periodonticum; Streptococcus intermedius; Wolinella recta.* This invention discloses compositions comprising polynucleotide probes able to hybridize to rRNA of these bacteria, especially the hypervariable regions of the 16S and 23S rRNA.

It is preferred that each specific probe hybridize to the rRNA of only one microbial species or type. Especially preferred are sequences complementary to the hypervariable regions of the 16S rRNA, as offered in Table 1, but these are not intended to be limiting. Alternative sequences are readily ascertainable using the sequencing methods disclosed herein. For example, sequences for the hypervariable regions from the 23S ribosomal RNA could be determined using the sequencing primers shown in Table 2. Using the methods disclosed herein, one of skill in the art could readily obtain alternative rRNA sequences with suitable specificity for use in this invention.

The nucleic acid sequence of the claimed probes include synthetically derived or recombinant nucleic acid sequences which have sufficient identity with the claimed sequences that they substantially hybridize with regions complimentary to the claimed probes. By "substantially", it is meant that under standard hybridization conditions of moderate stringency, percent hybridization can be shown to exceed 50% of the hybridization between perfectly complementary nucleic acid fragments.

By "compositions", it is meant that probes complementary to bacterial rRNA may be in a pure state or in combination with other probes. In addition, the probes may be in combination with salts or buffers, and may be in a dried state, in an alcohol solution as a precipitate, or in an aqueous solution.

The phrase "and combinations thereof," in the context of bacterial groups, refers to compositions of probes designed to detect one or more of the bacterial species stated. The probes may be a mixture of different probes capable of detecting a single species or two or more species, a mixture of different probes wherein the probes are each able to detect one or more species, or a homogeneous composition of a single probe. In the context of oligonucleotide sequences, the phrase "and combinations thereof" refers to a composition of copies of a single probe that may contain as a part of the probe one or more copies of a single oligonucleotide sequence or a mixture of the given sequences, or a mixture of probes that may contain as a part of the probes single or multiple copies of the given oligonucleotide sequences.

The terms oligonucleotide or polynucleotide probes are meant to include both double stranded and single stranded DNA or RNA. The terms also refer to synthetically or recombinantly derived sequences essentially free of non-nucleic acid contamination.

In addition to composition claims, methods are disclosed for the detection of a microbial cell associated with a medical disorder, in a sample obtained from the mouth of a human patient. These methods comprise the steps of: lysing the microbial cells to free the ribosomal RNA; contacting said ribosomal RNA, under hybridizing conditions, with polynucleotide probes capable of selectively hybridizing to the hypervariable regions of the ribosomal RNA of said microbial cell; and detecting hybridization complexes as an indication of the presence of the microbial cell in the sample. More specifically, there is disclosed herein the above method, where the bacteria detected are selected from the above list. Even more specifically, there is disclosed herein a method, as described above, in which the samples are assayed using at least two different groups of probes where each group is capable of hybridizing to a different hypervariable region of the ribosomal RNA of a single bacterium.

In addition to the above compositions and methods, there are disclosed herein diagnostic kits for use in determining the presence of bacteria which comprise a synthetic oligonucleotide probe complementary to hypervariable regions of the ribosomal RNA of a microbial cell associated with a human oral medical disorder.

The taxonomy of these bacteria is not static. Type cultures are available from the American Type Culture Collection (ATCC), Rockville, Md. As other bacteria are identified or other subtypes are differentiated from the above list, the disclosed invention readily provides methods for preparing probes of sufficient specificity for use in the detection and identification of these bacteria.

A composition of polynucleotide probes is also claimed wherein said probes comprise a segment of nucleic acid capable of selectively hybridizing to regions of ribosomal RNA of the bacteria having minimal secondary or tertiary interactions with adjacent nucleotides (open regions), said probes substantially binding only to open regions. By "substantially binding" it is meant that the probes do not comprise significant sequences that bind to regions that are available for hybridization only after heating, that is, regions with significant secondary and tertiary structure (closed regions). In practical terms, such probes will generally not comprise any more than 10 flanking nucleotides (either 5' or 3') which would bind to closed regions.

More specifically, compositions of polynucleotide probes complementary to open regions are claimed that are complementary to both hypervariable and conserved regions of bacterial rRNA.

A composition of polynucleotide probes is also claimed that hybridize to closed, conserved regions of bacterial rRNA.

Finally, methods are disclosed for the detection of microbial cells in a sample obtained from the mouth of a human patient. The method comprising the steps of: lysing the microbial cells to free the ribosomal RNA; contacting said ribosomal RNA, under hybridizing conditions, with polynucleotide probes capable of selectively hybridizing to open regions of the ribosomal RNA of said microbial cell; and detecting hybridization complexes as an indication of the presence of the microbial cell in the sample. More specifically, there is disclosed herein the above method, where the bacteria detected are selected from the above list. Even more specifically, there is disclosed herein a method, as described above, in which the samples are assayed using at least two different groups of probes where each group is capable of hybridizing to a different conserved region of the ribosomal RNA of a single bacterium.

DETAILED DESCRIPTION

This invention relates to the development of species specific nucleic acid probes complementary to the rRNA of species of oral bacteria associated with periodontal disease and other bacterial mediated diseases of the mouth. These probes are superior to probes complementary to genomic sequences because of their specificity and sensitivity. These probes have been selected for their ability to avoid cross-hybridizing with nonpathogenic bacterial species. Their superior properties are due to the ability to hybridize exclusively to hypervariable sequences of rRNA, which appear in hundreds to thousands of copies throughout each bacterial cell. The hypervariable regions of rRNA are sequences which are peculiar to a particular bacterial species or type. When compared with probes derived from whole genomic libraries, probes to rRNA, especially those complementary to hypervariable regions or rRNA, are advantageously sensitive and specific in their ability to detect low numbers of bacteria and to distinguish between bacterial species, types, and subtypes. It is preferred that the assays comprise capture oligonucleotides to two different hypervariable regions of the same bacterial ribosomal RNA. Such a format dramatically reduces the incidence of false negative results due to heterogeneity in the selected target regions. The methods disclosed herein have the advantage of being rapid assays. The disclosed methods are relatively simple to conduct, and they have a degree of reproducibility and accuracy that has heretofore not been achieved for bacterial pathogens of the mouth.

Sample Collection

Microbial specimens for use in this invention can be obtained from the ATCC for any of the bacteria listed in Table 1. For clinical studies, samples are obtained from teeth scrapings of subgingival plaque or from fluid taken from periodontal pockets with paper points of human patients suspected of having periodontal disease. The samples are dispersed in a buffer, which provides a biologically compatible solution, such as 150 mM NaCl, 20 mM Tris-HCl (ph 7.5), 10 mM EDTA, 10 mM EGTA, or 150 mM NaCl, 20 mM NaPO$_4$ (ph 7.5), 10 mM EDTA, 10 mM EGTA, and frozen until use. Prior to assay, the cells are optionally cultured in accordance with standard microbiological techniques, such as those described by Dzink, et al., J. Clin. Micro., 19:599, 1984. The bacteria are lysed in a lysis buffer containing N-acetylmuramidase (lysozyme). Lysing buffers are known in the art. EP 199,439; Potts, T. V. and Berry, Em. Internat. J. Sys. Bacter., 33:765–771 (1983); Bonta, Y., et al., J. Dent. Res., 64:793–798 (1985). Generally, these buffers are between ph 7.0 and 8.0, containing both chelating agents and surfactants. Heat denaturing is optional.

Alternatively, samples are dispersed and collected directly in a lysing solution that also functions as a hybridization solution, such as 3M guanidinium thiocyanate (GuSCN), 50 mM Tris (pH 7.6), 10 mM EDTA, 0.1% sodium dodecylsulfate (SDS), and 1% mercaptoethanol (Maniatis, T. et al. Molecular Cloning: A Laboratory Manual, Cold Spring Harbor, N.Y., 1982). Lysis is performed at 65° C. for 10 min.

Probes Complementary to the rRNA of Orally Pathoaenic Bacteria

This invention is directed to probes complementary to hypervariable regions of the rRNA sequence that are not conserved between bacterial species or types, and these probes can thus distinguish between species or types. Five sequences within 16S rRNA were derived using three universal oligonucleotide primers described by Lane et al., Proc. Natl. Acad. Sci., U.S.A., 82:6955–6959 (1985), and the following three oligonucleotide primers developed by us:

UP4B: 5'GCTGGCACGGAGTTAGCCG3';
UP8B: 5'CACGARCTGACGACARCCATGC3'; and
UP6B: 5'TACGGNTACCTTGTTACGAC.

The nomenclature for incompletely specified bases in the nucleic acid sequences are those recommended by the International Union of Biochemistry, Proc. Natl.

Acad. Sci., U.S.A. 83:4–8 (1986), which is herein incorporated by reference. For example, nucleotides designated R are interchangeable with guanosine, adenosine, or their analogs; nucleotides designated N means any of the natural nucleosides or their analogs may be interchanged at this position. Nucleotides designated Y are interchangeable with cytosine or thymine, nucleotides designated W are interchangeable with adenosine or thymine; nucleotides designated M are interchangeable with adenosine or cytosine.

These oligonucleotide primers are specific for conserved regions of the prokaryote 16S rRNA, and can be used to prime whole nucleic acid preparations without pretreatment with DNase or physical separations of RNA from DNA. Commercial preparations of reverse transcriptase, along with appropriate primer extension reactants for sequencing on electrophoretic gels, are used to obtain transcripts of cDNA complementary to the hypervariable regions of each pathogenic bacteria. The preferred sequencing methodology will use dideoxynucleotide chain termination. Similarly, oligonucleotide primers specific for conserved regions of the prokaryote 23S rRNA (Table 2) have been used to sequence nucleic acid preparations using known sequencing methodology.

The oligonucleotide probes shown in Table 2 are complementary to conserved regions of the prokaryote 16S and 23S ribosomal RNA, and will hybridize under hybridizing conditions to ribosomal RNA and its corresponding genomic DNA sequence. These universal oligonucleotide probes are also ideally suited to be utilized as signal oligonucleotides to DNA and especially RNA of all bacteria. In the multiple dipstick format (see later) the target nucleic acids are captured by probes specific for hyrpervariable regions while only one universal signal probe derived from the conserved regions of ribosomal RNA can be used to detect the nucleic acid from all the different pathogenic bacteria. In addition, it is possible to increase the strength of the signal by using more than one universal signal oligonucleotide probe.

After sequence analysis of the pathogens is complete for the 16S or 23S rRNA, the sequences can be compared by commercially available computer programs, such as the MicroGenie Program, sold by Beckman Instruments (Palo Alto, Calif.). Present programs are limited in that only two sequences can be compared at a time and all nucleotides are given equal importance. A more complex comparison can be made, but a more powerful computer (e.g., a Cray computer) is required. Waterman, M.S. Multiple Sequence Alignment by Consensus. Nuc. Acids. Res. 14 (1986), 9095–9102. The preferred method for selection requires alignment of multiple sequences and the identification of conserved blocks. Probes are then chosen to include maximum diversity (e.g., insertions or deletions instead of transitions). The probes may be either DNA or RNA, although DNA probes are preferred because they can be chemically synthesized.

The degree of complementary (homology) required for detectable binding with the rRNA of pathogenic bacteria will vary in accordance with the stringency of the hybridization medium and/or wash medium. The degree of complementary will optimally be 100 percent; however, it should be understood that minor variations in the rRNA may be compensated for by reducing the stringency of the hybridization and/or wash medium as described below. Thus, despite the lack of 100 percent complementary under reduced conditions of stringency, functional probes having minor base differences from their rRNA targets are possible. Therefore, under hybridization conditions of reduced stringency, it may be possible to modify up to 60% of a given oligonucleotide probe while maintaining an acceptable degree of specificity. In addition, analogs of nucleosides may be substituted within the probe for naturally occurring nucleosides. This invention is intended to embrace these species when referring to polynucleic acid probes.

To obtain large quantities of DNA or RNA probes, one can either clone the desired sequence using traditional cloning methods, such as described in Maniatis, T., et al. Molecular Cloning: A Laboratory Manual, Cold Spring Harbor, N.Y., 1982, or one can produce the probes by chemical synthesis using commercially available DNA synthesizers. An example of cloning would involve insertion of the cDNA for the ribosomal RNA into a replication vector, such as pBR322, M13, or into a vector containing the SP6 promotor (e.g., generation of single-stranded RNA using SP6 RNA polymerase), and transformation of a bacterial host. The DNA probes can be purified from the host cell by lysis and nucleic acid extraction, treatment with selected restriction enzymes, and further isolation by gel electrophoresis.

DNA probes may be chemically synthesized using commercially available methods and equipment. For example, the solid phase phosphoramidite method can be used to produce short probes of between 15 and 50 bases. For this invention, it is preferred to chemically synthesize short DNA probes using the Model 380B DNA Synthesizer from Applied Biosystems, Foster City, Calif., using reagents supplied by the same company. Probes may be comprised of the natural nucleotide bases or known analogs of the natural nucleotide bases, including those modified to bind labeling moieties.

The oligonucleotide sequences in Table 1 are representative of probes that hybridize with and detect specific regions of specific 16S rRNAs. The oligonucleotide sequences in Table 3 are representative of probes that hybridize with and detect hypervariable regions of specific 23S rRNAs, and should not be viewed as limiting. Probes may consist of these sequences or equivalent sequences, by themselves as a single unit for binding, or may be comprised of additional sequences not having the capacity to bind to non-pathogenic associated bacteria. Probes comprising more than the short sequences, as offered in Table 1, may have repeating units of the same sequence (e.g., concatemers of a sequence), a mixture of different sequences specific to one species of bacteria, and even a mixture of sequences that may be specific to one or more bacterial species associated with oral diseases.

If such probes are to contain concatemers of short sequences, said long probes will display the high hybridization specificity inherent in a "short" probe containing, for example, only 20 nucleotides. This concatemetic probe sequence could be contained within the cloning vector sequences and would have the structure given by the formula below. Alternatively, the concatemet having the formula [X—Y—Z]n as previously defined could be excised from the cloning vector with the appropriate restriction endonuclease.

Probes may be labeled by any one of several methods typically used to detect the presence of hybrid polynucleotides. The most common method of detection is the use of autoradiography with $^3H$, $^{125}I$ $^{35}S$ $^{14}C$, or $^{32}P$ labeled probes or the like. The choice of radio-active isotope depends on research preferences due to ease of synthesis, stability and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes, for example, by using DNA synthesizers, by nick translation with DNA polymerase I, by tailing radioactive DNA bases to the 3' end of probes with terminal deoxynucleotidyl transferase, by treating single-stranded M13 plasmids having specific inserts with the Klenow fragment of DNA polymerase in the presence of radioactive deoxynucleotides, dNTP, by transcribing from RNA templates using reverse transcriptase in the presence of radioactive deoxynucleotides, dNTP, or by transcribing RNA from vectors containing specific RNA viral promoters (e.g., SP6 promoter) using the corresponding RNA polymerase (e.g., SP6 RNA polymerase) in the presence of radioactive ribonucleotides rNTP.

The probes can be labeled using radioactive nucleotides in which the isotope resides as a part of the nucleotide molecule, or in which the radioactive component is attached to the nucleotide via a terminal hydroxyl group that has been esterified to a radioactive component such as inorganic acids, e.g., $^{32}P$ phosphate or $^{14}C$ organic acids, or esterified to provide a linking group to the label. Base analogs having nucleophilic linking groups, such as primary amino groups, can also be linked to a label.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or anti-genic compound can be used in combination with an anti-body.

Probes can also be labeled by direct conjugation with a label. For example, cloned DNA probes have been coupled directly to horseradish peroxidase or alkaline phosphotase, (Renz. M., and Kurz, K. A Colorimetric Method for DNA Hybridization. Nuc. Acids Res. 12:3435–3444, 1984) and synthetic olignucleotides have been coupled directly with alkaline phosphatase (Jablonski, E., et al., Preparation of Oligodeoxynucleotide-Alkaline Phosphaatase Conjugates and Their Use as Hybridization Probes. Nuc. Acids. Res. 14:6115–6128, 1986, and Li P., et al., Enzyme-linked Synthetic Oligonucleotide probes: Non-Radioactive Detection of Enterotoxigenic *Escherichia Coli* in Faeca Specimens. Nuc. Acids Res. 15:5275–5287 (1987).

Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g,, luminol.

Hybridization Conditions

Various hybridization solutions may be employed, comprising from about 20 to 60% volume, preferably 30%, of a polar organic solvent. A common hybridization solution employs about 50% v/v formamide, about 0.5 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, ficoll (about 300–500 kilodaltons), polyvinylpyrrolidone (about 250–500 kdal), and serum albumin. Also included in the typical hybridization solution will be unlabeled carrier nucleic acids from about 0.1 to 5 mg/ml, fragmented nucleic DNA, e.g., calf thymus or salmon sperm DNA, or yeast RNA, and optionally from about 0.5 to 2% wt./vol. glycine. Other additives may also-be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

An alternative hybridization solution may be employed comprising about 2 to 4M GuSCN, preferably 3M, about 0.01 to 0.1M Tris (pH range about 6.0 to 8.5), a detergent such as sodium dodecyl sulfate in concentrations of about 0.1 to 5% (w/v), and about 0.01 to 0.1M EDTA. Other additives may also be included such as carrier DNA or RNA, or protein such as bovine serum albumin or gelatin. Stringency of the hybridization solution can be adjusted by the addition of about 0 to 10% formamide, usually 5%.

The particular hybridization technique is not essential to the invention. Hybridization techniques are generally described in Nucleic Acid Hybridization: A Practical Approach, Ed. Hames, B. D. and Higgins, S. J., IRL Press, 1987; Gall and Pardue (1969), Proc. Natl. Acad. Sci., U.S.A., 63:378-383, and John, Burnstell and Jones (1969) Nature, 223:582–587. As improvements are made in hybridization techniques, they can readily be applied. One such improvement is the Subject of Serial No. 130,754, our docket 11652-5, filed on Dec. 9, 1987, incorporated herein by reference, which relates to the use of ultrasonic energy to enhance the rate of hybridization. This is an optional step which does not influence the specificity of the probes described herein.

The amount of labeled probe which is present in the hybridization solution may vary widely, depending upon the nature of the label, the amount of the labeled probe which can reasonably bind to the cellular target nucleic acid, and the stringency of the hybridization medium and/or wash medium. Generally, substantial excesses of probe over the stoichiometric amount of the target nucleic acid will be employed to enhance the rate of binding of the probe to the target DNA.

Various degrees of stringency of hybridization can be employed. As the conditions for hybridization become more severe, there must be a greater degree of complementary between the probe and the target for duplex formation to occur. The degree of stringency can be controlled by temperature, ionic strength, ph and the presence of a partially denaturing solvent such as formamide. For example, the stringency of hybridization is conveniently varied by changing the polarity of the reactant solution through manipulation of the concentration of formamide within the range of 0% to 50%. Temperatures employed will normally be in the range of about 20° to 80° C., usually 30° to 75° C. For probes of 15-50 nucleotides in 50% formamide, the optimal temperature range can vary from 22° to 65° C. With routine experimentation, one can typically define conditions which permit satisfactory hybridization at room temperature.

Assay test protocols for use in this invention are those of convention in the field of nucleic acid hybridization, and include both single phase, where the target and probe polynucleic acids are both in solution, and mixed phase hybridizations, where either the target or probe polynucleotides are fixed to an immobile support. The assay test protocols are varied and are not to be considered a limitation of this invention. A general review of single phase hybridization can be had from a reading of Nucleic Acid Hybridization: A Practical Approach, Ed. Hames, B. D. and Higgins, S. J., IRL Press, 1985, and Hybridization of Nucleic Acids Immobilized on Solid Supports, Meinkoth, J. and Wah, G., Analytical Biochemistry, pp. 238, 267-284, 1984. Mixed phase hybridizations are preferred.

Cultured colonies of the bacteria can be assayed using colony hybridization techniques, wherein the bacteria suspected of being orally pathogenic are plated and adsorbed onto a filter prior to exposure to the target polynucleotides (Grunstein and Hoghess, Colony Hybridization in Methods of Enzymology, Ed. Ray Wu, 1979, Vol. 68, pp. 379-409, and Proc. Natl. Acad. Sci. U.S.A., Vol. 72, No. 10:3961-3965, 1975). The colonies may also be identified by electrophoretically separating the nucleic acid and exposing the separated species to those probes designed to distinguish between species of pathogenic oral bacteria. Ribosomal RNA may be detected using the methods of Alwine, J. C., et al., Proc. Natl. Acad. Sci. U.S.A., Vol. 74(12): 5350-5354 (1977). Techniques for the electrophoretic separation of DNA, including ribosomal genomic regions, are described in WO 83/01073.

Methods for in situ hybridization are also applicable to this invention. In situ hybridization refers to the identification of bacterial cells using polynucleotide probes, wherein the intact cell is immobilized and provided as a target. The following two review articles provide an overview of the art of in situ hybridization: Singer, R. H., et al., Biotechniques, 4(3): 230-250 (1986), and haase, Al et al., Methods in Virology, Vol. VII, pp. 189-226 (1984), and are incorporated by reference herein.

Nucleic acids from GuSCN-lysed bacteria can be immobilized directly on to nitrocellulose or Nytran, and hybridized with the appropriate probe. The GuSCN-lysate is diluted with buffer containing formaldehyde, slotted to nitrocellulose and heated at 80° C. to denature the nucleic acids.

Regardless of the assay test protocol being used, the bacterial cells are to remain in contact with a hybridization solution at a moderate temperature for an extended period of time. In single phase assays, the double-stranded duplexes may be separated from single-stranded nucleic acid by $S_1$ nuclease digestion followed by precipitation of duplex molecules, or by selective binding to hydroxyapatite. In mixed phase assays, the support-immobilized nucleic acids is introduced into a wash solution having analogous concentrations of sodium chloride, buffers, and detergent, as provided in the hybridization solution. The time period for which the support is maintained in the wash solution may vary from several minutes to three hours or more.

Either the hybridization or the wash medium can be stringent. Typically, for mixed phase assays, it is the wash solution that most often determines the stringency and facilitates dissociation of mismatched duplexes. After rinsing the support at room temperature with a dilute buffered sodium chloride solution, the support may now be assayed for the presence of duplexes in accordance with the nature of the label.

Where the label is radioactive, the presence of probe can be detected in a scintillation counter. More conveniently, in mixed phase assays, the substrate can be dried and exposed to X-ray film in any number of conventional autoradiographic protocols.

Where the label is fluorescent, the sample is detected by first irradiating it with light of a particular wavelength. The sample absorbs this light and then emits light of a different wavelength which is picked up by a detector (*Physical Biochemistry*, Freifelder, D., W. H. Freeman & Co., pp. 537-542, 1982).

Where the label is a hapten or antigen, the sample can be detected by using antibodies. In these systems, a signal is generated by attaching fluorescent or enzyme molecules to the antibodies; in some cases the antibody is labeled with a radioactive probe. (Tijssen, P., *Practice and Theory of Enzyme Immunoassays*, Laboratory Techniques in Biochemistry and Molecular Biology, Burdon, R. H., van Knippenberg, Ph.H., Eds., Elsevier, pp. 9-20, 1985.)

One method of detection is enzymatic detection in conjunction with biotin. Although fluorescence is an alternative label, enzymatic labels, in combination with avidin or streptavidin such as biotinylated peroxidase or alkaline phosphatase, are preferred. Enzyme-conjugated avidin or streptavidin can also be used to directly bind the enzyme to the probe (Haase, et al., supra). Preferred enzymes are peroxidase or alkaline phosphatase. An especially preferred method utilizes enzymes directly conjugated to probes. The preferred enzymes are alkaline phosphatase and peroxidase. Methods for conjugating enzymes to oligonucleotides are known. Nucleic Acid Res., 14:6115-6128 (1986) and Nucl. Acid Res., 15:5275-5287 (1987).

The preferred assay protocol involves direct testing of samples without culturing. These protocols demand additional sensitivity for which the invention has particular application. Samples suspected of containing oral pathogenic bacteria are first subjected to a lysing solution, such as a buffered solution of detergent and a divalent metal chelator or a buffered chaotrophic salt solution containing a detergent, a reducing agent and a divalent metal chelator. The sample may be directly fixed to a support or further processed to extract nucleic acids. Released or extracted bacterial nucleic acid (including target nucleic acid) are fixed to a solid support, such as cellulose, nylon, nitrocellulose, diazobenzyloxymethyl cellulose, and the like.

In the preferred instance, the assay protocol is a sandwich-type assay. A primary component of a sandwich-type assay is a solid support. The solid support has adsorbed to it or covalently coupled to it immobilized nucleic acid probe that is unlabeled and complementary to one port, ion of the rRNA sequence. Preferred are those probes that hybridize to regions of the ribosomal RNA with minimal secondary and tertiary interactions, such as those listed in Table 4. The advantage of such probes is that the hybridization can be carried out without the additional step of heat denaturing the sample nucleic acid. The test sample suspected of containing oral pathogenic bacteria is then contacted with the solid support in a hybridization medium. Finally, a second soluble-labeled probe complementary to a different sequence of the rRNA of the pathogenic bacteria is hybridized to the rRNA that has formed a hybridization duplex with the immobilized nucleic acid probe on the solid support.

The presence of the bacteria is then determined in accordance with the label being used. It should be noted that the second probe can be added simultaneously with the test sample to the hybridization assay. In addition the second probe can hybridize to either a conserved or to a hypervariable region of the rRNA. Preferred are the probes derived from conserved regions of the ribosomal RNA with minimal secondary and tertiary interactions (Table 4), such as UP7B or UP9A for 16S ribosomal RNA, and UP12B or 23UPB for 23S ribosomal RNA. The advantage of such probes is that the hybridization can be carried out without the additional step of heat denaturing the nucleic acid. A general reference for various detection methods can be found in Hames, B. D. and Higgins, S. J., Nucleic Acid Hybridization, IRL Press, Oxford, 1985. References for sandwich assay with DNA probes are Dunn and Hassell Cell, Vol. 12, pp. 23-26, 1977, and Ranki, et al., U.S. Pat. No. 4,486,539.

The oligonucleotide or polynucleotide acid probes of this invention can be included in a kit which can be used to rapidly determine the presence or absence of oral pathogenic bacteria, especially the species disclosed in Table 1. The kit includes all components necessary to assay for the presence of these bacteria. In the universal concept, the kit includes a stable preparation of labeled probes to rRNA, hybridization solution in either dry or liquid form for the hybridization of target and probe polynucleotides, as well as a solution for washing and removing undesirable and nonduplexed polynucleotides, a substrate for detecting the labeled duplex, and optionally an instrument for the detection of the label.

A more specific embodiment of this invention embraces a kit that utilizes the concept of the sandwich assay. This kit would include a first component for the collection of samples from the mouths of patients, such as a scraping device or paper points, vials for containment, and buffers for the dispersement and lysis of the sample. A second component would include media in either dry or liquid form for the hybridization of target and probe polynucleotides, as well as for the removal of undesirable and nonduplexed forms by washing. A third component includes a solid support upon which is fixed or to which is conjugated unlabeled nucleic acid probe(s) that is(are) complementary to a part of either the 16S or 23S rRNA of the species of bacteria being tested. In the case of multiple target analysis more than one capture probe, each specific for its own ribosomal RNA, will be applied to different discrete regions of the dipstick. A fourth component would contain labeled probe that is complementary to a second and different region of the same rRNA strand to which the immobilized, unlabeled nucleic acid probe of the third component is hybridized. The probe components described herein include coordinations of probes in dry form, such as lyophylized nucleic acid or in precipitated form, such as alcohol precipitated nucleic acid or in buffered solutions. The label may be any of the labels described above. For example, the probe can be biotinylated using conventional means and the presence of a biotinylated probe can be detected by adding avidin conjugated to an enzyme, such as horseradish peroxidase, which can then be contacted with a substrate which, when reacted with peroxidase, can be monitored visually or by instrumentation using by a colorimeter or spectrophotometer. This labeling method and other enzyme-type labels have the advantage of being economical, highly sensitive, and relatively safe compared to radioactive labeling methods. The various reagents for the detection of labeled probes and other miscellaneous materials for the kit, such as instructions, positive and negative controls, and containers for conducting, mixing, and reacting the various components, would complete the assay kit.

The following examples are offered by way of illustration and not by limitation.

EXAMPLE 1

A. preparation of rRNA

Bacterial cells are resuspended in a lysis solution (20 mg/ml lysozyme, 25% sucrose, 50 mM Tris, pH 8, 10 mM EDTA), and incubated at 37° C. for 30 min. Sodium dodecylsulfate (1-2% w/v) and pronase E (1 mg/ml) or proteinase K (200 μg/ml) are added, and the solution is incubated 30 min at 37° C. The lysates are extracted twice with. phenol:chloroform (1:1, v/v) and then precipitated with ethanol. Nucleic acid is pelleted, washed with 70% v/v ethanol, and resuspended to approximately 1 mg/ml in 1× TE buffer (10 mM Tris, pH 8, 1 mM EDTA). Resuspended nucleic acid is stored at −70° C.

B. Oligonucleotide Sequencing Primers

Universal sequencing primers (UP) for rRNA were as described by Lane, et al., Proc. Natl. Acad. Sci. U.S.A., 82, 6955-6959 (1985). Three additional primers, herein designated UP4B, UP5B and UP6B, and having the sequences UP4B: GCTGGCACGGAGTTAGCCG;
UP8B: CACGARCTGACGACARCCATGC;
UP6B: TACGGNTACCTTGTTACGAC;

were designed and utilized for sequencing.

C. Sequencing Reactions

The protocol for sequencing is a modification of the dideoxynucleotide-terminated chain elongated method described by Sanger, F., et al., Proc. Natl. Acad. Sci. U.S.A., 74, 5463-5467 (1977), as adapted for rRNA templates by Lane, et al. Proc. Natl. Acad. Sci. U.S.A., 82, 6955-6959 (1985). Sequencing primers were radioactively labeled with 32P-ATP using T4 polynucleotide kinase (50 uCi 32P-ATP, 3000 Ci/mMol, per 300 ng oligo and 10 units of kinase). The radioactively labeled primers were ethanol precipitated and resuspended in water to 30 ng/ml.

A standard sequencing reaction is set up as follows. Two μl of primer are added to 3 μl of a solution of bacterial nucleic acid (0.5-25 mg/ml), 2 μl 5× HYB buffer (500 mM KCl, 250 mM Tris-HCl, pH 8.5), and 3 μl of H₂O. The mix is heated at 100° C. for 2 min, then cooled to room temperature. To this mix is added 4 μl of 5× RT buffer (250 mM Tris-Hcl, pH 8.3, 250 mM KCl, 50 mM dithiothreitol, 50 mM MgCl₂), 5 μl H₂O, and 2 μl reverse transcriptase (200 U/μl, Bethesda Research Laboratories, Gaithersburg, Md). Three μl aliquots are pipetted into 2 μl deoxynucleotide/dideoxynucleotide mixes (A: 17 μM dATP, 300 μM dCTP, 330 μM dGTP, 330 μM TTP, 125 μM ddATP; C: 330 μM dATP, 17 μM dCTP, 330um dGTP, 330 μM TTP, 125 μM ddCTP; G: 330 μM dATP, 330 μM dCTP, 17 μM dGTP, 330 μM TTP, 250 μM ddGTP; T: 330 μM dATP, 330 μM dCTP, 330 μM dGTP, 17 μM TTP, 125 μM ddTTP). The reactions are incubated at 43° C. for 15 min. Two μl of chase (330 μM dATP, dCTP, dGTP, TTP, plus 400 units of reverse transcriptase) are added to each reaction. The reactions are incubated for an additional 15 min at 43° C., and terminated by the addition of 6 μl loading solution (95% formamide, 2.5% xylene cyanol, 2.5% bromphenol blue). Reaction products were electrophoresed on 8% polyacrylamide denaturing gels and visualized by autoradiography. The sequencing reactions can also be performed using unlabeled sequencing primer and [35S] dATP under reaction conditions similar to those described

D. Synthesis and Purification of Synthetic Oligonucleotide Probes

Oligonucleotides were synthesized on an Applied Biosystems DNA synthesizer Model 380B via β-cyanoethylphosphoramidite chemistry. The oligonucleotides were purified by preparative polyacrylamide gel electrophoresis or by high pressure liquid chromatography and eluted as detailed in Applied Biosystems User Bulletin No. 13: "Evaluation and Purification of Synthetic Oligonucleotides," Nov. 9, 1984. See Table 1 for preferred sequences.

E. Isolation of Nucleic Acid from Bacterial Culture or Subgingival plaque Samples The following procedure is applicable to either a curette scraping or cultured bacteria: 500 μl of sample (stored at −70° C.) is thawed with the following steps to be conducted immediately. 100 ng of an unrelated carrier oligonucleotide (24 bases) is added to the sample if it is a plaque sample or a dilute bacterial sample. 250 μl of sucrose lysis buffer (75% (w/v) sterile sucrose, 10 mM EDTA, 10 mM EGTA, 50 mM Tris-HCl (pH 8.0), is added to the sample and vortexed briefly. 50 μl of freshly made lysozyme (10 mg/ml in 0.25× bacterial sucrose lysis buffer; Sigma Chemical), is added and the sample incubated for 15 min at 37° C. 75 μl of 10% SDS is then added and the sample vortexed briefly. 75 μl of Pronase E (10 mg/ml, Sigma Chemical; self-digested as per Maniatis, et al., Molecular Cloning: A Laboratory Manual) is added, the sample vortexed briefly and incubated at 37° C. for 30 min. The sample is extracted two times with phenol:chloroform:isoamyl alcohol (24:24:1, v/v/v), saving the aqueous phase. If the interphase is not clear, it can be extracted again with chloroform and the aqueous phase saved. The sample is then concentrated by lyophilization to 300 μl, to which 150 μl of a sterile 7.5M NH4OAc solution is added, and followed by 1.12 ml of 95% ethanol. The sample is then mixed and stored at −70° C. for 30 min or longer to precipitate the nucleic acid, and the pellet is recovered by centrifugation for 10 min at 4° C. The nucleic acid pellet is washed once with 1.5 ml of 95% ethanol, dried briefly, and then resuspended in 400 μl of sterile TE buffer (10 mM Tris-HCl pH 7.5, 0.1 mM EDTA).

F.a) Immobiliation of Nucleic Acid onto Nytran Membranes

The extracted microbial nucleic acids are immobilized onto Nytran as follows: 380 μl of nucleic acid (at less than 6 μg/380 μl) in TE and 20 μl of 200 mM Pipes (pH 7.42) are mixed to give a final concentration of 20 mM. Pipes. The sample is heated to 100° C. for 90 sec, quickly chilled in a ice/water bath, and then applied to a Nytran membrane using a slot blot apparatus from Schleicher and Schuell (Keene, N.H.). Slotting should be finished within 20 min of the heat treatment. The slots are washed with 200 μl of 10× SSC (1.5M NaCl, 0.15M sodium citrate pH 7.0), the Nytran membrane with immobilized nucleic acid baked at 80° C. for 1 hour, and the Nytran membrane stored at room temperature between blotting paper.

F.b) Direct immobilization of cell lysates to nitrocellulose membranes

A cell pellet of cultured bacteria or a plaque sample is resuspended in 100 ul of 3M GuSCN, 2% sarkosyl w/v, 50 mM Tris-HCl (ph 7.6), 10 mM EDTA, and 1% v/v mercaptoethanol and incubated at room temperature for 10 min. To this solution is added 0.3 volumes of 20× SSC, followed by 0.2 volumes of 37% formaldehyde, and incubation at 55° C. for 15 min. Serial dilutions are made in 15× SSC and the nucleic acid solutions slotted onto nitrocellulose (prewetted with water and soaked in 6× SSC for 10 min). The filters are baked at 80° C. under vacuum for 2 hours and stored at room temperature between blotting paper.

G. Hybridization

Procedure A

Probes are labeled with $^{32}P$ by polynucleotide kinase as per Maniatis, T. et al. Molecular Cloning: A Laboratory Manual, Cold Spring Harbor, N.Y., 1982, (200 ng of oligonucleotide, 60 μCi $^{32}P$-ATP, and 40 units of T4 polynucleotide kinase in a 25 μl volume) and purified by ethanol precipitation and Elutip-D chromatography (Scheicher and Schuell). Alternatively, probes are synthesized with an ethylamine group at the 5' end, biotinylated with NHS-LC-biotin (Pierce Chemical Co., Rockford, Ill.), and purified by Elutip-D chromatography. Nucleic acids, immobilized on Nytran or nitrocellulose membranes, are hybridized with 5 ng/ml of oligonucleotide probe in 0.6M NaCl, 90 mM Tris-HCl (pH 8.0), 10 mM EDTA, 5× Denhardt's solution, 30% deionized formamide, 0.1% SDS, and 100 μl/ml fragmented yeast RNA at 42° C., or in 0.9M NaCl, 90 mM Tris-HCl (ph 8.0), 10 mM EDTA, 5× Denhardt's solution, 0.1% SDS, and 100 μg/ml fragmented yeast RNA at 50° C. The hybridizations are carried out in 50 ml polypropylene tubes or with sealed "Micro-Seal" plastic bags (Dazey Corp., Industrial Airport, Kans.) on a rotary shaker at the appropriate temperature for 1 hour or longer. The membranes are first washed in 0.09M NaCl, 9 mM Tris-HCl (ph 8.0), EDTA, and 0.1% SDS at room temperature, and then washed in the same wash buffer at 50° C. (=stringent wash). An alternate stringent wash can be conducted with 3.1M tetraethylammonium bromide, 50 mM Tris-HCl (ph 8.0), 2 mM EDTA, and 0.1% SDS at 29° C. (this procedure requires a 0.9M NaCl, 90 mM Tris-HCl (pH 8.0), 10 mM EDTA pre-wash prior to the tetraethylammonium bromide wash).

Procedure B

Nucleic acids immobilized on membranes are hybridized with 5 ng/ml oligonucleotide probe in 3M GuSCN, 5% formamide, 50 mM Tris (pH 7.6), 10 mM EDTA, 2% sarkosyl for 0.5 to 24 hours as described in procedure A. The membrane is washed twice for 2 min with a solution containing 0.09M NaCl, 9 mM Tris-HCl (pH 8.0), 1 mM EDTA, and 0.1% SDS at room temperature. When $^{32}$P labeled probes were used, nucleic acids were visualized by autoradiography. The use of biotinylated probes required the incubation with streptavidin-alkaline phosphatase or streptavidine-peroxidase followed by color development as described in Example 2.

H. Detection of Hybridized Probe

Hybridized probe labelled with $^{32}$P was detected by autoradiography. Biotinylated probes were detected by the Detek-alk kit (avidin-alkaline phosphatase; Enzo Biochem, New York, N.Y.) or the DNA detection kit (streptavidin/biotinylated alkaline phosphatase polymer; Bethesda Research Labs, Gaithersburg, Md.).

I. Identification of Synthetic Oligonucleotide Probes Complementary to Regions with Minimal Secondary and Tertiary Interaction The chemical and enzymatic accessibility of nucleotides along the predicted secondary structure of the 16S and 23S ribosomal RNA have been observed. Moazed, D. et al. (1986) J. Mol. Biol. 187:399–416. Noller, H. F. et al. (1981) Nucleic Acids Res. 9:6167–6189. However, the accessibility of these regions to complementary oligonucleotide probes is not predictable. Lasater, L. S. et al. (1988) Biochemistry 28:4687–4695. Regions of the ribosomal RNA with minimal secondary and tertiary interactions are defined by solution hybridization and sandwich assay methods. For example, purified ribosomal RNA (1–5 ug) was hybridized with $^{32}$P-labelled complementary oligonucleotide probes (5–10 ng), such as those in Table 1 or Table 2, in 0.09M NaCl, 9 mM Tris-HCl (ph 8.0), and 1 mM EDTA, or 3M GuSCN, 2% sarkosyl, 50 mM Tris-HCl (pH 7.6), 10 mM EDTA, 1% mercaptoethanol, and 5% formamide.

Following hybridization for 15 min to 1 hour, the sample was subjected to agarose gel electrophoresis to separate the 16S and 23S ribosomal RNA subunits, and the oligonucleotide probe:rRNA hybrids visualized by autoradiography. Oligonucleotide probes which showed hybridization specific to their respective ribosomal RNA subunit were further tested in the sandwich assay format. In this format the test oligonucleotide probe was covalently attached to a solid support. Target ribosomal RNA was hybridized in the presence of the test oligonucleotide and $^{32}$P-labelled signal oligonucleotide probes, such as UP7B or UP9A for 16S ribosomal RNA, or UP12B or 23UPB for 23S ribosomal RNA, using the GuSCN hybridization solution described above in Procedure B. After hybridization for 2–15 hours, the solid support was washed of unhybridized nucleic acid, and the amount of ribosomal RNA captured by the test oligonucleotide probe quantitated by liquid scintillation counting.

EXAMPLE 2

The direct conjugation of alkaline phosphatase to the oligonucleotide probes will eliminate several steps required in the assay procedures using oligonucleotide probes (e.g., biotinylated probes) which are indirectly linked with enzymes.

Direct conjugation of alkaline phosphatase to a short probe involves conjugation via heterobifunctional reagents. The synthetic probe is synthesized as described herein with a linker arm reagent attached to the terminal 5'-hydroxyl.

An aminohexyl linker arm with a terminal amino group is attached to the 5'-hydroxyl of the synthetic oligodeoxynucleotide as the last step in its synthesis on an automated DNA synthesizer. The reagent used for linker arm introduction is 6-(methoxytritylamino)hexyl 2-cyanoethyl N,N-diisopropylphosphoramidite, prepared from 6-aminohexanol in a manner similar to the synthesis of the 3-(methoxytritylamino)propyl methyl N,N-diisopropylphosphoramidite, as described by B. A. Cormoily, Nucl. Acids Res., 15:3131 (1987). The linker arm is attached to the probe, and the deprotected probe purified in a method similar to the methods described in the Connolly reference.

The oligonucleotide first is derivatized with the thiol-reactive agent N-succinimidyl(4-iodoacetyl)aminobenzoate ("SIAB") through the amino linker arm. The SIAB-oligonucleotide is prepared by adding 1.2 mg SIAB to 300 μg of the oligonucleotide, incubating for one hour at room temperature, and desalting over a G-25 column equilibrated with 20 mM sodium phosphate (pH 6.0), 5 mM EDTA. This probe derivative can be coupled to alkaline phosphatase which is modified as described below.

Alkaline phosphatase is thiolated with dithiobis(succinimidylpropionate) ("DSP") by adding 800 μg DSP to 4 mg alkaline phosphatase. The reaction is allowed to proceed for 30 min at room temperature. The reaction mixture then is treated with dithiothreitol for 15 min at room temperature to reduce the disulfide, and desalted over a G-25 column equilibrated with 20 mM sodium phosphate (pH 6.0).

The SIAB-oligonucleotide is mixed with the DSP-alkaline phosphatase at a oligonucleotide:alkaline phosphatase ratio of 4:1. 5M NaCl is added to the reaction to bring the final NaCl concentration to 3M, and the pH is adjusted to 7.5 with 0.1 volume 1M Tris (pH 7.5). The coupling reaction is allowed to proceed overnight (16 hours), then stopped with N-ethylmaleimide (2 μl of 10 ng/ml). The conjugate is separated from free oligonucleotide by gel filtration on a P-100 column, and free alkaline phosphatase is removed by DEAE cellulose chromatography.

Horseradish peroxidase (HRP) is first treated with NaIO$_4$ (IO4: HRP, 160:1) to oxidize the sugar diols. After 15 min at room temperature the IO$_4$ is removed by gel filtration over Sephadex G-25, and the material concentrated to less than 20 mg/ml in 1 mM NaOAc (pH 4.5). The concentrated hRP is then used to resuspend a pellet of oligonucleotide with a 5'-hexylaminelinker arm. Following resuspension, the pH of the reaction mix is adjusted to 9.5 with carbonate buffer and NaBH$_3$CN is added to 50 mM. The reaction is allowed to proceed for 16 to 20 hours at room temperature and the products separated by HPLC using a GF-250 column (Dupont). The probe-enzyme conjugates are tested in the following ways. *Fusobacterium nucleatum* or *Bacteroides gingivalis* genomic DNA was serially diluted into human placental DNA, heat denatured, and applied to slots on a Nytran membrane. Bg-1B:HRP (100 ng/ml in 30% formamide, 0.6M NaCl, 90 mM Tris-HCl (pH 8.0), 10 mM EDTA, and 0.1% SDS)

was hybridized to the immobilized DNA for 1 hour at room temperature, and washed in 0.45M NaCl, 45 mM Tris-HCl pH 8.0, 5 mM EDTA pH 8.0, and 0.1% SDS for 20 min at 50° C. The wash solution was removed, and substrate solution (100 mM HEPES Citrate-phosphate buffer (pH 6.5), 90 μM 3-methyl-2-benzothiazolinone hydrazone, 6 mM 4-methoxynaphthol, and 4 mM $H_2O_2$, or 19 mM 9-aminoethylcarbazol, 100 mM NaOAc pH 4.5, and 7 mM $H_2O_2$) was added. Hybridized probe was detected as a blue or brown precipitate, respectively, on the *Bacteroides gingivalis* DNA slots.

Fn-1B:alkaline phosphatase or Bg-1B:alkaline phosphatase were hybridized for 1 hour at room temperature to the Nytran membranes as above. The membranes were washed as above and substrate solution (0.6 mM nitro-blue tetrazolium in 70% dimethylformamide, 0.6 mM 5-bromo-4-chloro-3-indolyl phosphate in 0.1M Tris-HCl pH 9.5, 0.1M NaCl, 50 mM $MgCl_2$) was added. Hybridized probe was detected as a blue precipitate on F. nucleatum or B. gingivalis DNA slots, respectively.

Sandwich hybridizations with the Bg-1B:HRP probe was performed as follows. Varying concentrations of Bg-5B:SIAB probe in PBS (150 mM NaCl, 10 mM sodium phosphate pH 7.01) were immobilized to cysteamine-derivatized Pall Immunoaffinity membranes (Pall Corporation, East Hills, N.Y.). The membranes were made by conjugating Pall Immunoaffinity membranes (0.2μ pore size) with 10 mM cystamine in PBS and then washing and treating the cystamine-derivatized membranes with DTT (10 mM for 30 min at 25° C.) to produce a cysteamine-derivatized membrane. Non-covalently immobilized probe was removed from these membranes by heating at 90° C. in PBS. The Pall:Bg-5B membranes were hybridized with a DNA target (complementary to Bg-5B) and Bg-1B:HRP(Bg-1B:5 'GAA-TAACGGGCGATACGAGTATTGATTGAATG-TACCGTAAGAATAAGCAT CGG 3') for 30 min in 0.6M NaCl, 30% formamide, 90 mM Tris-HCl (pH 8.0), 10 mM EDTA, 0.1% SDS at 42° C. The complex was washed in 0.09M NaCl, 9 mM Tris (pH 8.0), 1 mM EDTA at 50° C. for 20 min. The wash solution was decanted and the 4-chloro-methoxynapthol substrate added. After a 15 min incubation, at room temperature, the hybridized Bg-1B:HRP probe was detected as a blue precipitate on the Pall:Bg5B membrane. Purified Bg 16S rRNA hybridized in a like manner also was detected by sandwich hybridization with Bg-1B:HRP and Pall:Bg5B.

EXAMPLE 3

Different concentrations of *B. gingivalis* were lysed with 3M GuSCμg, 5% formamide, 50 mM Tris-HCl (pH 7.6), 10 mM EDTA, 2% sarkosyl, and 1% mercaptoethanol. Pall membranes with 0.1 μg of immobilized Bg-5B oligonucleotide were immersed into the lysate and hybridized for 0.5 to 24 hours at room temperature. The membranes were washed with a solution containing 0.09M NaCl, 9 mMTris-HCl (pH 8.0), 1 mM EDTA, and 0.1% SDS. The Pall:Bg-5B:rRNA membranes were hybridized again in the GuSCN/formamide lysis solution containing 10–100ng/ml biotinylated signal oligonucleotide and hybridized from 0.5 to 24 hours. The biotinylated signal oligonucleotides used were UP7B, UP9A, and UP3A. The membranes were washed with a solution containing 0.09M NaCl, 9 mM Tris-HCl (pH 8.0), 1 mM EDTA, and 0.5% SDS. The membranes were then incubated with the strepavidin conjugate of alkaline phosphatase (or horse-radish peroxidase) in 0.18M NaCl, 18 mM Tris-HCl (pH 8.0), 2 mM EDTA, 0.5% SDS, and 0.1% gelatin at room temperature for 15 to 60 min. After the incubation the membranes were washed three times for 1 min each with 0.18M NaCl, 18 mM Tris-HCl (pH 8.0), 2 mM EDTA, and 0.5% SDS, then two times for 1 min each with 0.18M NaCl, 18 mM Tris-HCl (pH 8.0), and 2 mM EDTA, and finally once with appropriate substrate buffer. Color was developed for the two enzymes as described in Example 2. The hybridized signal probe was detected as brown and blue spots for alkaline phosphatase and horse radish peroxidase, respectively. Depending on the enzyme and hybridization conditions, detection of $1 \times 10^7$ *B. gingivalis* cells was observed. Signal intensity is dependent upon the number of biotinylated signal oligonucleotides used, and is 3× less when only one signal oligonucleotide is present in the assay.

EXAMPLE 4

A test kit for the detection of oral pathogenic bacteria will contain all of the required components for the collection, processing, and evaluation of several samples, as well as the associated instructions and patient data collection cards.

Product Insert. The Product Insert will contain complete written instructions for patient sampling and evaluation. The instructions will follow the procedures of Example 3.

Data Card. A Data Card will be included for the recording of minimal baseline data for each patient, such as patient identification, site of collection, and test results.

Currettes. Currettes for sampling by scraping.

Endodontic Points. Endodontic points (paper points) for collection of each sample to be tested are also included. After cleansing the supragingival surfaces by wiping with gauze, the point will be used to rub the bacteria from the subgingival surface of the tooth to be sampled and to collect bacteria by absorption of saliva, gingival fluid, and gingival plaque.

Lysing Reagent. Each point with the collected sample will be placed immediately into a numbered tube of Lysing Reagent which will lyse the bacteria and release the bacterial nucleic acids.

Probe/Enzyme Reagent. A standard aliquot of Probe labeled by a ligand with or directly conjugated to an Enzyme Reagent is added to each tube of Lysing Reagent to initiate the hybridization reaction between the pathogen nucleic acid targets and the signal oligonucleotide probes derived from conserved regions of the ribosomal RNA sequences.

Dipstick Device. An individual Dipstick Device containing site(s) with pathogen-specific DNA probes covalently immobilized to the solid support and having space for marking and identifying each site tooth sampled, is inserted immediately into each tube containing the hybridization mixture and incubated at room temperature.

Wash Reagent. Each Dipstick Device is removed from the hybridization mixture and washed with the Wash Reagent, using the bottle provided.

Enzyme Substrate Reagent. The Dipstick Devices are placed collectively into the Enzyme Substrate Reagent bottle and developed for several minutes to 1 hour at room temperature. Each Dipstick Device is washed again with the Wash Reagent to remove excess background color.

Reference Card. Color development is visualized and compared with a Reference Card, indicating the pathogens providing a positive signal.

TABLE 1

Oligonucleotides specific for bacteria associated with periodontal disease.

| | | Oligonucleotide Primers Used to Derive Sequence |
|---|---|---|
| *Bacteroides gingivalis* | | |
| Bg-1B | 5'CAATACTCGTATCGCCCGTTATTC3' | UP4B/1B |
| Bg-4B | 5'GTATAAAAGAAGTTTAMAATCCTT3' | UP4B/1B |
| Bg-6B | 5'CCTTAGGACAGTCTTCCTTCACGC3' | UP4B/1B |
| Bg-3B | 5'CTGTGGAAGCTTGACGGTATATCG3' | UP2B |
| Bg-SB | 5'GGTTTTCACCATCAGTCATCTACA3' | UPSB |
| Bg-7B | 5'ATTACCCTAGTGCGCCCCTTGCGG3' | UP6B |
| Bg-5B* | 5'CCGATGCTTATTCTTACGGTACAT3' | UP4B/1B |
| *Actinobacillus* (ex. *Haemophilus*) *actinomycetemcomitans* | | |
| Aa-3B | 5'ATTTAACGTCAATTTGGCATGCTA3' | UP4B/1B |
| Aa-2B | 5'CTTCGGGCACYAGGGCTAAACCCC3' | UP2B |
| Aa-4B | 5'ACCCATCTCTGAGTTCTTCTTCGG3' | UPSB |
| Aa-5B | 5'GTGGTAAACGCCCCCCTCTCGGTT3' | UP6B |
| Aa-10B | 5'TGGCATGCTATTAACACACCAACC3' | UP4B/1B |
| *Bacteroides intermedium* - Type I | | |
| Bi-1B | 5'GGTCCTTATTCGAAGGGTAAATGC3' | UP4B/1B |
| Bi-3B | 5'CACGTGCCCCACTTTACTCCCCAA3' | UP4B/1B |
| Bi-6B | 5'TAGCCGCTAACGCCAGGCGCTAAC3' | UP2B |
| Bi-2B | 5'CCCTAGGYGCGCTCCTCGCGGTTA3' | UP6B |
| Bi-5B | 5'GAGTCAACATCTCTGTATCCTGCG3' | UP8B |
| Bi-4B* | 5'TTGCCCTAGGTCGCTCCTCGCGGT3' | UP6B |
| *Bacteroides intermedium* - Type II | | |
| 2Bi-3B | 5'AGACGCCCCGAAGGAAGCCTATGT3' | UP8B |
| 2Bi-1B | 5'ATGAGGTACATGCAATGGCGCACA3' | UP4B |
| 2Bi-2B | 5'CGTGCGCCAATTTATTCCCACATA3' | UP4B |
| *Bacteroides forsythus* | | |
| Bf-1B | 5'CACAAGGTACATGCAATAAAATAC3' | UP4B |
| Bf-2B | 5'CGTATCTCATTTTATTCCCCTGTA3' | UP4B |
| Bf-5B | 5'AGCTCTCACTCTCCGTCGTCTACA3' | UP4B |
| Bf-6B | 5'AATACACGTATCTCATTTTATTCC3' | UP4B |
| Bf-3B | 5'GAAGAAAGCTCTCACTCTCCGTCG3' | UP8B |
| Bf-4B | 5'CTGTAGAGCTTACACTATATCGCA3' | UP2B |
| *Eikenella corrodens* | | |
| Eik-4B | 5'GTACGCTACTAAGCAATCAAGTTG3' | UP2B |
| Eik-1B | 5'TTAGGTACCGTCAGCAAAAAGTGG3' | UP4B |
| Eik-2B | 5'GCACTTCCCTTTTCTTCCCTAACA3' | UP4 |
| Eik-3B | 5'TACCGTGGCAAGCGGGCTCCTTGC3' | UP6B |
| Eik-5B | 5'CTTCCGTCTCTGGAAGGTTCCGTAC3' | UP8B |
| *Fusobacterium nucleatum/periodonticum* | | |
| Fn-1B | 5'GTCATCGTGCACACAGAATTGCTG3' | UP7B |
| Fn-2B | 5'GTTGGTACCGTCATTTTTTTCTTC3' | UP4B |
| Fn-3B | 5'AGGTTTCCCCGAAGGCACTGAAAC3' | UP8B |
| Fn-4B | 5'TCAGACTCTCGGTCCATTGTCCAA3' | UP4B/1B |
| Fn-6B | 5'AAACATCTCTGTCTCATTCCTAAG3' | UP8B |
| *Wolinella recta* | | |
| Wr-1B | 5'GTACCGTCATAATTCTTTCCCAAG3' | UP4B |
| Wr-2B | 5'GGACCATAACCGGTTTGGTATTTG3' | UP6B |
| Wr-3B | 5'GCATTACTGCCTCGACTAGCGAAG3' | UP2B |
| Wr-6B | 5'CTTGGGTACCGTCATAATTCTTTCC3' | UP4B |
| *Streptococcus intermedius* | | |
| Si-1B | 5'GTACCGTCACAGTATGAACTTTCC3' | UP4B |
| Si-2B | 5'TTCTCACACTCGTTCTTCCTTAAC3' | UP4B |
| Si-3B | 5'TTTCCATTCTCACACTCGTTCTTC3' | UP4B |

*Designed to hybridize to both Type I and II, Note Overlaps with Bi-2B

TABLE 2

Universal Primers for Sequencing and Conserved Signal Oligonucleotides.

| | | E. coli base position |
|---|---|---|
| 16S rRNA oligonuclectide probes | | |
| UP1B* | 5'GWATTACCGCGGCKGCTG3' | 519–536 |
| UP4B | 5'GCTGGCACGGAGTTAGCCG3' | 504–522 |
| UP7B | 5'GTATTACCGCGGCTGCTG3' | 519–536 |
| UP2B* | 5'CCGTCAATTCATTTAAGTTT3' | 907–926 |
| UP2D | 5'CCCGTCWATTCMTTTGAGTTTT3' | 906–927 |
| UP2A | 5'CCCGTCAATTCATTTGAGTTTT3' | 906–927 |

TABLE 2-continued

Universal Primers for Sequencing and Conserved Signal Oligonucleotides.

| | | E. coli base position |
|---|---|---|
| UP3B* | 5'ACGGGCGGTGTGTRC3' | 1392–1406 |
| UP3A | 5'TGACGGGCGGTGTGTACAA3' | 1390–1408 |
| UP9A | 5'CTGCTGCCTCCCGTAGGAGT3' | 338–357 |
| UP15B | 5'GGGTATCTAATCCKGTTYGCTCC3' | 775–797 |
| UP20B | 5'GACTACYMGGGTATCTAATCC3' | 785–805 |
| UP21A | 5'TTAAACCACATGYTCCWCCGCTTG3' | 936–959 |
| 23S RRNA oligonucleotide probes | | |
| UP12B | 5'TYGATTGGCMTTTCACCCC3' | 775–793 |
| UP13B | 5'GGGGTTCTTTTCGCCTTTCC3' | 468–487 |
| 23UPA | 5'CTTAGATGCTTTCAGC3' | 2744–2759 |
| 23UPB | 5'CCGGTCCTCTCGTACTA3' | 2653–2669 |
| 23UPC | 5'GGACCGAACTGTCTCACGACGTTCT3' | 2587–2611 |
| 23UPD | 5'GACCGCCCCAGTCAAACT3' | 2241–2258 |
| 23UPE | 5'CCCGACAAGGAATTTCGC3' | 1933–1950 |
| 23UPF | 5'CCTTCTCCCGAAGTTACGG3' | 1685–1703 |
| 23UPG | 5'GACCAGTGAGCTATTACGC3' | 1091–1109 |
| 23UPH | 5'TTCGGGGAGAACCAGCTA3' | 803–820 |
| 23UPJ | 5'TTCGCTCGCCGCTACT3' | 241–256 |
| 23UPM | 5'GTTATAGTTACGGCCGCCGTTTAC3' | 1897–1920 |

*Equivalent to ribosomal RNA sequencing primers described by Lane et al.

TABLE 3

Bacteria Specific Oligonucleotide Probes Derived from 23S Ribosomal RNA Sequences.

| | | Oligonucleotide Primers Used to Derive Sequence |
|---|---|---|
| *Bacteroides gingivalis* | | |
| Bg23-1 | 5'TTGGGAGCCGGTTTACATCCTTAT3' | 23UPF |
| Bg23-2 | 5'GTACGGGTAACACAGAAATATGCT3' | 23UPF |
| Bg23-3 | 5'CTCAAATTGCTTTTTTGATAGCTT3' | 23UPE |
| Bg23-4 | 5'GACTATATACCTCAAATTGCTTTT3' | 23UPE |
| Bg23-5 | 5'TTCTCTTGACGATGACTCCTCCTC3' | 23UPE |
| Bg23-6 | 5'CCTACACATCTGATGCCAAATACA3' | 23UPD |
| *Fusobacterium nucleatum* | | |
| Fn23-1 | 5'TCGATTAAGACTCCATCTTAATAG3' | 23UPJ |

TABLE 4

Probes Derived from Hypervariable and Conserved Regions of the 16S and 23S Ribosomal RNA which are Free of Secondary and Tertiary Interactions.

| | Oligonucleotide probe | E. coli base position |
|---|---|---|
| 16S RRNA Hypervariable Regions | | |
| Aa-4B | 5'ACCCATCTCTGAGTTCTTCTTCGG3' | 990–1030 |
| Aa-10B | 5'TGGCATGCTATTAACACACCAACC3' | 445–475 |
| Bg-6B | 5'CCTTAGGACAGTCTTCCTTCACGC3' | 395–430 |
| Bg-8B | 5'GGTTTTCACCATCAGTCATCTACA3' | 990–1030 |
| Bg-5B | 5'CCGATGCTTATTCTTACGGTACAT3' | 475–505 |
| Bi-3B | 5'CACGTGCCCCACTTTACTCCCCAA3' | 445–475 |
| Bi-5B | 5'GAGTCAACATCTCTGTATCCTGCG3' | 990–1030 |
| 2Bi-2B | 5'CGTGCGCCAATTTATTCCCACATA3' | 445–475 |
| Eik-4B | 5'GTACGCTACTAAGCAATCAAGTTG3' | 828–865 |
| Eik-2B | 5'GCACTTCCCTTTTCTTCCCTAACA3' | 445–475 |
| Eik-5B | 5'CTTCCGTCTCTGGAAGGTTCCGTAC3' | 990–1030 |
| Fn-2B | 5'GTTGGTACCGTCATTTTTTTCTTC3' | 445–475 |
| Fn-4B | 5'TCAGACTCTCGGTCCATTGTCCAA3' | 445–475 |
| Fn-6B | 5'AAACATCTCTGTCTCATTCCTAAG3' | 990–1030 |
| Wr-1B | 5'GTACCGTCATAATTCTTTCCCAAG3' | 445–475 |
| Wr-6B | 5'CTTGGGTACCGTCATAATTCTTTCC3' | 445–475 |
| 23S RRNA Hypervariable Regions | | |
| Bg23-2 | 5'GTACGGGTAACACAGAAATATGCT3' | 1570–1620 |
| Bg23-4 | 5'GACTATATACCTCAAATTGCTTTT3' | 1800–1830 |
| Bg23-6 | 5'CCTACACATCTGATGCCAAATACA3' | 2085–2120 |
| 16S RRNA Conserved Regions | | |
| UP2D | 5'CCCGTCWATTCMTTTGAGTTTT3' | 906–927 |
| UP3A | 5'TGACGGGCGGTGTGTACAA3' | 1390–1408 |
| UP7B | 5'GTATTACCGCGGCTGCTG3' | 519–536 |
| UP9A | 5'CTGCTGCCTCCCGTAGGAGT3' | 338–357 |
| UP20B | 5'GACTACYMGGGTATCTAATCC3' | 785–805 |
| UP21A | 5'TTAAACCACATGYTCCWCCGCTTG3' | 936–959 |
| 23S RPNA Conserved Regions | | |

TABLE 4-continued

Probes Derived from Hypervariable and Conserved Regions of the 16S and 23S Ribosomal RNA which are Free of Secondary and Tertiary Interactions.

| Oligonucleotide probe | | E. coli base position |
| --- | --- | --- |
| UP12B | 5'TYGATTGGCMTTTCACCCC3' | 775–793 |
| 23UPB | 5'CCGGTCCTCTCGTACTA3' | 2653–2669 |
| 23UPJ | 5'TTCGCTCGCCGCTACT3' | 241–256 |
| 23UPM | 5'GTTATAGTTACGGCCGCCGTTTAC3' | 1897–1920 |

What is claimed is:

1. A composition of polynucleotide probes for the detection of bacteria associated with periodontal disease, wherein said probes consist of a segment of nucleic acid capable of hybridizing, under hybridizing conditions, to conserved regions of ribosomal RNA of the bacteria with the provision that any additional nucleotides covalently bound to said segment do not hybridize under said conditions to nucleic acids of bacteria found in the human mouth, and further wherein said nucleic acid segment is selected from a group consisting of:
5'GCTGGCACGGAGTTAGCCG3';
5'GGGTATCTAATCCKGTTYGCTCC3';
5'GGGGTTCTTTTCGCTTTCC3';
5'CTTAGATGCTTTCAGC3';
5'GGACCGAACTGTCTCACGACGTTCT3';
5'GACCGCCCCAGTCAAACT3';
5'CCCGACAAGGAATTTCGC3';
5'CCTTCTCCCGAAGTTACGG3';
5'GACCAGTGAGCTATTACGC3';
5'TTCGGGGAGAACCAGCTA3';
5'TGACGGGCGGTGTGTACAA3';
5'TTAAACCACATGYTCCWCCGCTTG3';
5'TYGATTGGCMTTTCACCCC3';
5'CCGGTCCTCTCGTACTA3';
5'TTCGCTCGCCGCTACT3';
5'GTTATAGTTACGGCCGCCGTTTAC3';
and combinations thereof wherein K represents G or T, M represents A or C, W represents A or T, and Y represents C or T.

2. A composition of polynucleotide probes for the detection of bacteria associated with a periodontal disease, wherein said probes consist of a segment of nucleic acid capable of hybridizing, under hybridizing conditions, to open conserved regions of ribosomal RNA of the bacteria having minimal secondary or tertiary interactions with adjacent nucleotides, said probes substantially binding only to open conserved regions wherein the nucleic acid segment is selected from the group consisting of:
5'TTAAACCACATGYTCCWCCGCTTG3';
5'TYGATTGGCMTTTCACCCC3';
5'CCGGTCCTCTCGTACTA3';
5'TTCGCTCGCCGCTACT3';
5'GTTATAGTTACGGCCGCCGTTTAC3';
and combinations thereof wherein M represents A or C, W represents A or T, and Y represents C or T.

* * * * *